(12) United States Patent
Weinstein et al.

(10) Patent No.: US 9,913,602 B2
(45) Date of Patent: Mar. 13, 2018

(54) SYSTEM AND METHOD FOR MEASURING BLOOD PARAMETERS

(71) Applicant: ORSENSE LTD., Petah Tikva (IL)

(72) Inventors: Aharon Weinstein, Ramat HaSharon (IL); Yosef Gandelman, Ashdod (IL)

(73) Assignee: ORSENSE LTD., Petah Tikva (IL)

( * ) Notice: Subject to any disclaimer, the term of this patent is extended or adjusted under 35 U.S.C. 154(b) by 207 days.

(21) Appl. No.: 14/413,078

(22) PCT Filed: Jul. 2, 2013

(86) PCT No.: PCT/IL2013/050557
§ 371 (c)(1),
(2) Date: Jan. 6, 2015

(87) PCT Pub. No.: WO2014/006612
PCT Pub. Date: Jan. 9, 2014

(65) Prior Publication Data
US 2015/0157247 A1   Jun. 11, 2015

Related U.S. Application Data

(60) Provisional application No. 61/668,719, filed on Jul. 6, 2012.

(51) Int. Cl.
*A61B 5/1455* (2006.01)
*A61B 5/00* (2006.01)

(52) U.S. Cl.
CPC ........ *A61B 5/14552* (2013.01); *A61B 5/0059* (2013.01); *A61B 5/6826* (2013.01);
(Continued)

(58) Field of Classification Search
CPC .............. A61B 5/14551; A61B 5/1455; A61B 5/14553; A61B 5/0059; A61B 5/0075
See application file for complete search history.

(56) References Cited

U.S. PATENT DOCUMENTS 4,406,289 A * 9/1983 Wesseling .......... A61B 5/02255
600/483
5,776,071 A 7/1998 Inukai et al.
(Continued)

FOREIGN PATENT DOCUMENTS

CN    1224600 A    8/1999
CN    1418072 A    5/2003
(Continued)

*Primary Examiner* — Eric Winakur
*Assistant Examiner* — Marjan Fardanesh
(74) *Attorney, Agent, or Firm* — Browdy and Neimark, P.L.L.C.

(57) ABSTRACT

The present invention provides techniques for measuring one or more parameters of a subject using a probe having an optical assembly configured and operable for applying optical measurements to a measurement location in a subject and generating optical measured data indicative thereof comprising at least one of pulsatile and occlusion measurements, a pressure system configured and operable for controllably applying pressure to the subject in the vicinity of the measurement location and measuring pressure inside the pressure system and generating pressure data indicative thereof, and a control system configured and operable for receiving and processing the pressure data to identify whether the optical measured data is valid, and for processing the valid optical measured data and determining at least one relation between the valid optical measured data and the corresponding pressure data indicative of at least one parameter of the subject.

30 Claims, 8 Drawing Sheets

(52) U.S. Cl.
 CPC .......... *A61B 5/6838* (2013.01); *A61B 5/7221* (2013.01); *A61B 5/7275* (2013.01)

(56) References Cited

U.S. PATENT DOCUMENTS

| | | | |
|---|---|---|---|
| 6,154,667 A * | 11/2000 | Miura | A61B 5/14552 |
| | | | 600/323 |
| 6,190,325 B1 | 2/2001 | Narimatsu | |
| 6,196,974 B1 | 3/2001 | Miwa | |
| 6,400,972 B1 | 6/2002 | Fine | |
| 6,983,178 B2 | 1/2006 | Fine et al. | |
| 8,419,649 B2 | 4/2013 | Banet et al. | |
| 2002/0161305 A1 | 10/2002 | Oka | |
| 2003/0212316 A1 | 11/2003 | Leiden et al. | |
| 2004/0230107 A1 * | 11/2004 | Asada | A61B 5/0084 |
| | | | 600/335 |
| 2006/0287603 A1 * | 12/2006 | Bartnik | A61B 5/0261 |
| | | | 600/504 |
| 2007/0232936 A1 * | 10/2007 | Mann | A61B 5/0215 |
| | | | 600/486 |
| 2007/0282182 A1 * | 12/2007 | Messerges | A61B 5/0059 |
| | | | 600/324 |
| 2009/0234210 A1 * | 9/2009 | Matlock | A61B 5/14552 |
| | | | 600/344 |
| 2010/0331635 A1 * | 12/2010 | Wang | A61B 5/145 |
| | | | 600/309 |
| 2011/0046464 A1 * | 2/2011 | Debreczeny | A61B 5/14551 |
| | | | 600/335 |

FOREIGN PATENT DOCUMENTS

| | | | |
|---|---|---|---|
| CN | 1798520 A | 7/2006 | |
| WO | 0145553 | 6/2001 | |
| WO | 0196872 | 12/2001 | |
| WO | 2004/105596 A1 | 12/2004 | |
| WO | 2007020647 | 2/2007 | |
| WO | WO 2011045138 A1 * | 4/2011 | ......... A61B 5/02241 |

* cited by examiner

SYSTEM AND METHOD FOR MEASURING BLOOD PARAMETERS

TECHNOLOGICAL FIELD

The disclosure herein concerns techniques for measuring blood parameters in an organ of a living subject.

BACKGROUND

Non-invasive measurement techniques are increasingly accepted for the measurement of blood parameters (e.g., blood oxygen saturation). These techniques are particularly favorable since they do not require withdrawal of blood samples from the examined subject. For example, non-invasive optical measurement techniques are based on detection of light transmitted through (or reflected from) the a tissue/organ of the examined subject, and employ spectrophotometric measurements to determine the presence of various blood constituents based on known spectral behaviors of these constituents.

Many of the optical non-invasive techniques utilize an optical device or probe configured to attach to a finger of a subject, and an optical assembly for irradiating the finger with light and detecting its light response (e.g., measuring the intensity of light transmitted/reflected through/from the radiated finger). Conventional devices, such as pulse oximeters which are the generally accepted standard of everyday clinical practice, provide for measuring enhanced optical pulsatile signals caused by the changes in the volume of blood flowing through a fleshy medium (e.g., finger).

It is known that for blood parameters other than oxygen saturation, e.g., glucose concentration, significant difficulties are encountered due to their spectral absorption behavior in red and near infrared regions which is not as remarkable as for oxygenized hemoglobin. Hence, the main limitations on the way of expanding the non-invasive techniques to measurements different from pulse oximetry are associated with the limited selectivity of the absorption based method.

Occlusion-based techniques are disclosed in U.S. Pat. No. 6,400,972, WO 01/45553 and WO 01/96872, all assigned to the assignee of the present application, wherein over-systolic pressure is applied to the blood perfused fleshy medium with a normal blood flow (also referred to herein as pulsatile state) so as to create a state of temporary blood flow cessation at the measurement location. In these techniques measurements are taken using different wavelengths of incident radiation and/or different polarization states of detected light at timely separated sessions during a time period including a cessation time in which a blood flow cessation state (also referred to herein as occlusive state) is maintained. Due to the cessation of the blood flow, a condition of artificial blood kinetics is achieved, with the optical characteristics of the blood associated with the light response being different from those at normal (i.e., pulsatile) blood kinetics. It was found that owing to the effect of the artificial kinetics, the optical characteristics of blood changes dramatically, such that they differ from those of the fleshy medium with a normal blood flow by about 25 to 45%, and sometimes even by 60%. Hence, the accuracy (i.e., signal-to-noise ratio) of the technique based on the artificial kinetics as well as selectivity of the optical measurements can be substantially improved when compared with those based on measurements of the blood parameters at natural/normal kinetics.

In another non-invasive measurement technique, described in WO 2007/020647, also assigned to the assignee of the present application, measurements are performed by applying an external electromagnetic field to a measurement location in a subject and detecting at least two responses from which data indicative of the detected response is generated. The measurements are carried out under normal blood flow conditions for generation of first measured data indicative of a first time variation of the response for each of the at least two parameter values, and under a condition of artificial kinetics for generation of second measured data indicative of a second time variation of the response for each of said at least two parameter values. The first and second measured data are processed to determine a first relation between the first time variations for the different parameter values and a second relation between the second time variations for these different parameter values. The first and second relations are then utilized to determine the at least one blood and/or tissue related parameter.

U.S. Pat. Nos. 5,776,071, 6,190,325 6,196,974, and US Patent application No. 2002/161305, describe blood-pressure monitoring apparatuses including a measuring device using an inflatable cuff to apply a pressing pressure to a body portion of a living subject and measure at least one blood-pressure value of the living subject by changing the pressing pressure of the inflatable cuff.

U.S. Pat. No. 8,419,649 describes a method and apparatus for continuous measurement of blood pressure, based on pulse transit time, which does not require any external calibration. A body-won sensor is used to measure blood pressure and other vital signs, and wirelessly transmit them to a remote monitor. A network of disposable sensors, typically placed on the patient's right arm and chest, connect to the body sensor and measure a time-dependent electrical waveform, optical waveform, and pressure waveform. The disposable sensors typically include an armband that features an inflatable bladder coupled to a pressure sensor, at least 3 electrical sensors, and an optical sensor attached to a wrist-worn band.

GENERAL DESCRIPTION

The present invention relates to a method, device and system, for non-invasively measuring blood parameters in a subject. A principle feature of embodiments of the present invention is the combining of optical and fluid pressure measurement data obtained non-invasively from an organ/tissue of the examined subject, and using the same to determine one or more parameters of the subject including tissue and blood parameters such as concentration of one or more analytes in blood as well as oxygen saturation.

The inventors of the present invention found out that the accuracy and reliability of optically measured blood parameters may be substantially improved by combining the optically measured data with pressure fluctuations concurrently measured in the same examined tissue/organ on which the optical measurement are being carried out. More particularly, it is now understood that the pressure fluctuations measured in the examined organ reflects volumetric blood changes in the examined organ, which may be combined with the measured optical data to improve the accuracy of determined parameters (e.g., analytes levels) and/or to determine the validity and reliability of the optical measurement data.

For example, in possible embodiments of the present application the measured pressure data is used in a data processing stage for diminishing interfering effects introduced in the measured optical data and/or to validate the reliability of the measured optical data and ensure that it may be used to determine the one or more blood parameters.

In some possible embodiments of the present disclosure the transmission/reflection of light through/from the examined organ is measured during at least one of normal blood flow conditions (i.e., pulsatile state) and occlusive blood conditions (occlusive state), and pressure changes in the examined organ are simultaneously measured during at least one of the pulsatile and the occlusive states. The measured data may be then processed to determine relations between the optical measurement data in the pulsatile and/or occlusive states and the measurement pressure data obtained from the examined organ during at least one of the pulsatile and occlusive states. The determined relations provide an indication as to the one or more blood parameters of interest (e.g., presence and/or concentration of one or more analytes).

For example and without being limiting, in some possible embodiments of the present application the examined organ is illuminated in the occlusive state by one or more light signals having predetermined wavelengths associated with said one or more blood parameters (hereinafter also referred to as inspection signals), and by one or more other light signals having reference wavelengths (hereinafter also referred to as reference signals). The examined organ is also illuminated by the one or more optical inspection signals and the one or more optical reference signals in the pulsatile state. The transmissions/reflections of the inspection and reference light signals during the occlusive and pulsatile blood states are measured and processed to provide optical measured data associated with the one or more inspection signals used during the pulsatile state and during the occlusive state, and optical reference signal data associated with the one or more reference signals used during the pulsatile state and during the occlusive state. Pressure in the examined organ is measured simultaneously or almost simultaneously with optical measurements (i.e., within at least partially overlapping optical and pressure measurement sessions), where the optical measurements taken during the pressure measurements may be only with the use of reference wavelength(s), and may include at least one of the pulsatile and occlusive states. The measured pressure is processed/analyzed to provide pressure data. The optical measured data and/or the pressure data may be then processed to determine relations therebetween in each of the pulsatile and occlusive blood states, said relations being indicative of the one or more blood parameters of interest.

Optionally, the pressure measurements may be carried out during time intervals that are different (or having some partial overlap) from the time intervals during which the optical measurements are taken. However, in some of the embodiments hereof which employ reference wavelength signals e.g., for calculating parametric slopes (PS), the pressure measurement and the reference optical measurement are taken simultaneously during substantially the same time periods. It is however noted that in possible embodiments of the present application the pressure is measured in only part of the occlusion and/or pulsatile states time periods, and/or with partial overlap therewith, and not necessarily during the same time periods during which optical measurements of the various inspection wavelength signals are taken. Yet, in possible embodiments the pressure is measured during time periods in which optical measurements of reference wavelength signals are taken. However, the reference wavelength signals are not needed for determination of AC/DC ratios.

Optionally, the pressure data may be used to determine validity of the measured optical signals. For examples, the optical signals measured during the pulsatile and/or occlusive states may be invalidated whenever determining vascular volumetric instabilities in the examined organ/tissue based on the pressure data. Alternatively, the processing of the measured optical signals may be modified whenever such vascular volumetric instabilities are detected. For example and without being limiting, the processing of the measured optical data may be modified to include only data portions corresponding to the optical signals measured during time periods of the pulsatile and/or occlusive states in which vascular volumetric stability has been observed.

In some embodiments, the processing of the measured optical data includes determining a relation between measured inspection signal data associated with at least one of the predetermined inspection wavelengths and measured optical reference signal data associated with at least one of the reference wavelengths in at least one of the pulsatile and the occlusive blood states, determining a relation between pressure data and the optical reference signal data for the common measurement time period in at least one of the pulsatile and the occlusive blood states, and determining the one or more blood parameters based on the determined relations.

The measured optical data includes a time function of the measured intensity of transmitted and/or reflected light in response to the illumination. In other words, the measured optical data includes at least one pairs of time functions for the inspection and reference wavelengths, where the same reference wavelength may be used in different pairs (i.e., only inspection wavelengths are different). The analysis of the optical measured data includes determination of at least one relation between the inspection and reference time functions, e.g., a parametric slope of transmission/reflection signal changes for one wavelength as a function of transmission/reflection signal changes for the other wavelength.

In one aspect the present application provides a system for measuring one or more parameters of a subject. The system may comprise a probe for attaching to the subject, where the probe carries an optical assembly configured and operable for applying optical measurements to a measurement location in the subject and generating optical measured data indicative thereof, a pressure system configured and operable for controllably applying pressure to the subject in the vicinity of the measurement location, measuring pressure inside the pressure system, and generating pressure data indicative thereof, and a control system configured and operable for receiving and processing the pressure data, and processing the optical measured data and determining at least one relation between the optical measured data and the corresponding pressure data, said at least one relation being indicative of at least one parameter of the subject.

The optical measurements may comprise at least one of pulsatile (e.g., oxymetry) and occlusion measurements.

Optionally, the control system is configured and operable for processing the pressure data to identify whether the optical measured data is valid, and accordingly, processing the valid optical measured data and determining at least one relation between the valid optical measured data and the corresponding pressure data, said at least one relation being indicative of at least one parameter of the subject. The control unit may be also used to identify motion artifacts in at least one of the pressure measurement data and the optical measurement data and filter out from the measurement data parts associated with the motion artifacts.

In some possible embodiments the pressure system comprises at least one expandable element carried by the probe and being configured and operable to be shiftable between its unexpanded and expanded states to thereby selectively permit a pulsatile blood state and create an occlusive blood state in the measurement location respectively, and a pressure sensor coupled to the at least one expandable element and being configured and operable to generate the pressure data indicative of pressure in the vicinity of the measurement location in the subject while being in at least one of said pulsatile and occlusive blood states.

The system may further comprise a pressure source fluidly coupled to the at least one expandable element and configured and operable to apply a fluid pressure operable to shift the expandable element into the expanded state. Optionally, the system may also comprise a pressure vessel fluidly coupled to at least one of the pressure source and the at least one expandable element and configured and operable to hold a volume of pressurized fluid.

Optionally, the volume of the pressure vessel is greater than a summation of volumes of the at least one of the expandable element and of elements in the system coupled thereto (i.e., elements connected to/via the pressure manifold). For example and without being limiting, the volume of the pressure vessel may be at least twice the summation of all the other volumes being in fluid communication therewith.

The system may comprise a barometric pressure sensing element configured and operable to measure atmospheric pressure of an environment external to the system and generate barometric data indicative thereof, the control unit is configured and operable to use the barometric data to compensate effects of said atmospheric pressure on the pressure measurement data. Optionally, a temperature sensor may be also used to measure temperature at the measurement location and generate temperature data indicative thereof, the control unit may thus configured and operable to use the temperature data to correct influence of temperature on at least one of the pressure and optical measurement data.

In some embodiments the probe defines a probing cavity for holding a body portion of the subject such as to bring a measurement location in the body portion into a measurement position, the probe being configured and operable to adjust a size of the probing cavity to geometry of the body portion.

Optionally, at least one expandable element is movably disposed inside the adjustable probing cavity. A locking mechanism may be used in the probe configured and operable to immobilize movable parts associated with the adjustable cavity. For example, the locking mechanism may include at least one inflatable member fluidly coupled to a pressure source and configured and operable to receive fluid pressure therefrom and responsively change the locking mechanism into a locking state for immobilizing the movable parts.

The probe may comprise a housing having bottom and upper hollow portions telescopically movable one relative to the other. Movement of the hollow portions of the housing may define the size of the probing cavity, and the locking mechanism may be configured and operable to stop movement of these hollow portions. Optionally, the housing comprises a movable plate elastically coupled to the bottom hollow portion and fixedly coupled to the upper hollow portion.

In some embodiments there is provided a system for measuring one or more blood parameters of an examined tissue, comprising at least one expandable element configured and operable to permit a pulsatile blood state in the tissue in an unexpanded state thereof, and to apply an occlusive blood state in the tissue in an expanded state thereof, an optical assembly configured to generate intensity signals indicative of intensity of at least one light signal passing through the examined tissue in at least one of the pulsatile and occlusive blood states, a pressure sensor coupled to the at least one expandable element configured and operable to generate pressure signals indicative of pressure in the tissue being in at least one of the pulsatile and occlusive blood states, and a processor configured to process the intensity and pressure signals, identify motion artifacts in at least one of the intensity and pressure signals and filter out parts of the signals associated with the motion artifacts, and calculate at least one relation between the filtered signals, where the relation being indicative of the at least one blood parameter.

In another aspect, the present application provides a method for measuring at least one blood parameter in a subject. The method comprising receiving optical measured data indicative of at least one of a pulsatile and occlusive blood states in a measurement location in the subject, receiving pressure data indicative of vascular volumetric changes in the measurement location in the subject measured while in the at least one of the pulsatile and occlusive blood states during which the measured data is obtained, and processing the optical measured data and the pressure data and determining at least one relation between the measured optical data and pressure data, said at least one relation being indicative of the at least one blood parameter.

In yet another application, there is provided a system for measuring one or more blood parameters of an examined tissue, the system comprising at least one expandable element configured and operable to permit a pulsatile blood state in the tissue in an unexpanded state thereof, and to apply an occlusive blood state in the tissue in an expanded state thereof, an optical assembly configured to generate intensity signals indicative of intensity of at least one light signal passing through the examined tissue in at least one of the pulsatile and occlusive blood states, a pressure sensor coupled to the at least one expandable element configured and operable to generate pressure signals indicative of pressure in the tissue being in at least one of the pulsatile and occlusive blood states, and a processor configured to process the intensity and pressure signals and calculate at least one relation therebetween, the at least one relation being indicative of said at least one blood parameter.

The optical measured data may be indicative of passage of at least two light signals of different wavelengths through the examined tissue in the at least one of the pulsatile and occlusive blood states. Optionally, at least one of the wavelengths is a reference wavelength and the pressure data is indicative of vascular volumetric changes during application of light of said reference wavelength.

BRIEF DESCRIPTION OF THE DRAWINGS

In order to understand the invention and to see how it may be carried out in practice, embodiments will now be described, by way of non-limiting example only, with reference to the accompanying drawings, in which like reference numerals are used to indicate corresponding parts, and in which.

It is noted that the embodiments exemplified in the figures are not intended to be in scale and are in diagram form to facilitate ease of understanding and description.

DETAILED DESCRIPTION OF EMBODIMENTS

The present disclosure aims to provide techniques for measurement of blood parameters (e.g., analytes) based on spectroscopy techniques (e.g., occlusion spectroscopy technology in the red/near-infrared light spectrum range). It should be understood that the term "spectroscopy" is used herein to refer to optical measurements carried out with more than one wavelength, although determination of spectra itself might not be needed. The techniques disclosed herein are based on the oximetry principles (e.g., pulse oximetry) which are combined with techniques for evaluation of vascular volumetric status to provide reliability and accuracy of blood properties determination. Typically, in oximetry techniques, light passing through the tissue of the examined finger is transmitted/reflected out of the tissue being modulated by the heartbeat waveform, and the difference in the light absorption by oxyhemoglobin and deoxyhemoglobin enables calculation of Oxygen saturation using only two light signals of different wavelengths. Contrary to oxygen saturation (SpO2), which provides a relative result, hemoglobin (Hb) and glucose concentrations are absolute values (gr/dL) that need to be differentiated from the effect of interfering parameters, such as blood volume, finger size and SpO2. Thus the non-invasive measurement of parameters concentrations is significantly more complex, and needs additional information that is very difficult to extract from the natural pulsatile signal.

Occlusion spectroscopy technology typically overcomes this hurdle by the generation of an artificial bio-physical signal, resulting from temporarily occluding the blood flow to the measurement site.

In some embodiments of the present disclosure the measurements are performed using an annular probe assembly (i.e., ring-like probe mountable onto a patient's finger) comprising inflatable elements (also referred to herein as occluding cushions e.g., pneumatically operated cuffs), with which an over-systolic pressure is applied over a portion of the finger (e.g., the finger base phalange) placed within an annular probing zone of the annular probe. A multi-wavelength light source and a highly sensitive detector may be used to record the transmission/reflection of light through/ from the measurement location in the finger, and a sensitive pressure sensor coupled to the inflatable elements is used to record pressure changes during one or more of the optical inspection sessions.

It is however noted that any organ that can be placed in an annular probe design of the present disclosure may be used for determining the blood and/or tissue parameters. For example, in some possible embodiments of the present application the probe device is designed to receive a wrist of a baby.

Figure 1:
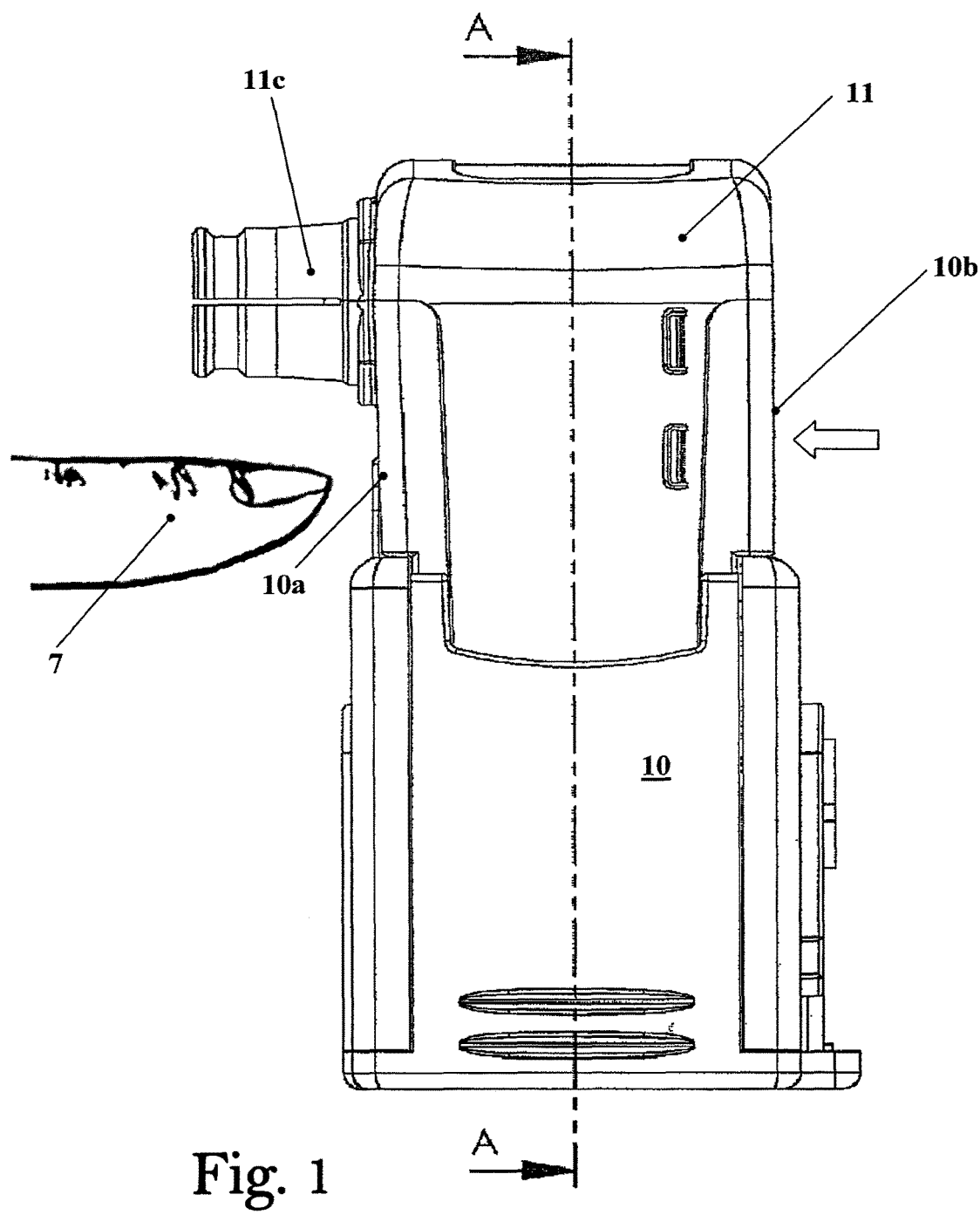
FIG. 1 shows a side view of a probe used for carrying out measurements on a finger of a subject in some possible embodiments of the present disclosure.

FIG. 1 depicts a side view of a probing device 10 usable with some possible embodiments of the present disclosure for carrying out various measurements over a portion of a finger 7 of a subject. Probing device 10 includes a housing 11 comprising a cylindrically-like cavity defined by an annular opening 10a at one side of the housing through which finger 7 may be introduced into the cavity (10c, shown in FIG. 2) such that a portion of the finger 7 becomes enclosed thereinside. A corresponding annular opening 10b may be provided in the opposite side of the housing 11 being aligned with the annular opening 10a, such that distal end (tip) of finger 7 (e.g., distal and/or intermediate phalanges) may be passed through, and out of, the cylindrical cavity of the probing device 10.

As will be described below, probing device 10 is configured to carry out various measurements over the portion of finger 7 (e.g., proximal phalange) enclosed inside it. Male connector 11c protruding laterally form housing 11 is used to communicate the probing device 10 with an external system configured to operate the probing device using electric signals and also to apply fluid pressure onto the finger, and conduct various measurements and obtain the results measured during one or more measurement sessions carried out in the same or preferably different blood condition states of the finger tissue enclosed therein.

Figure 2:
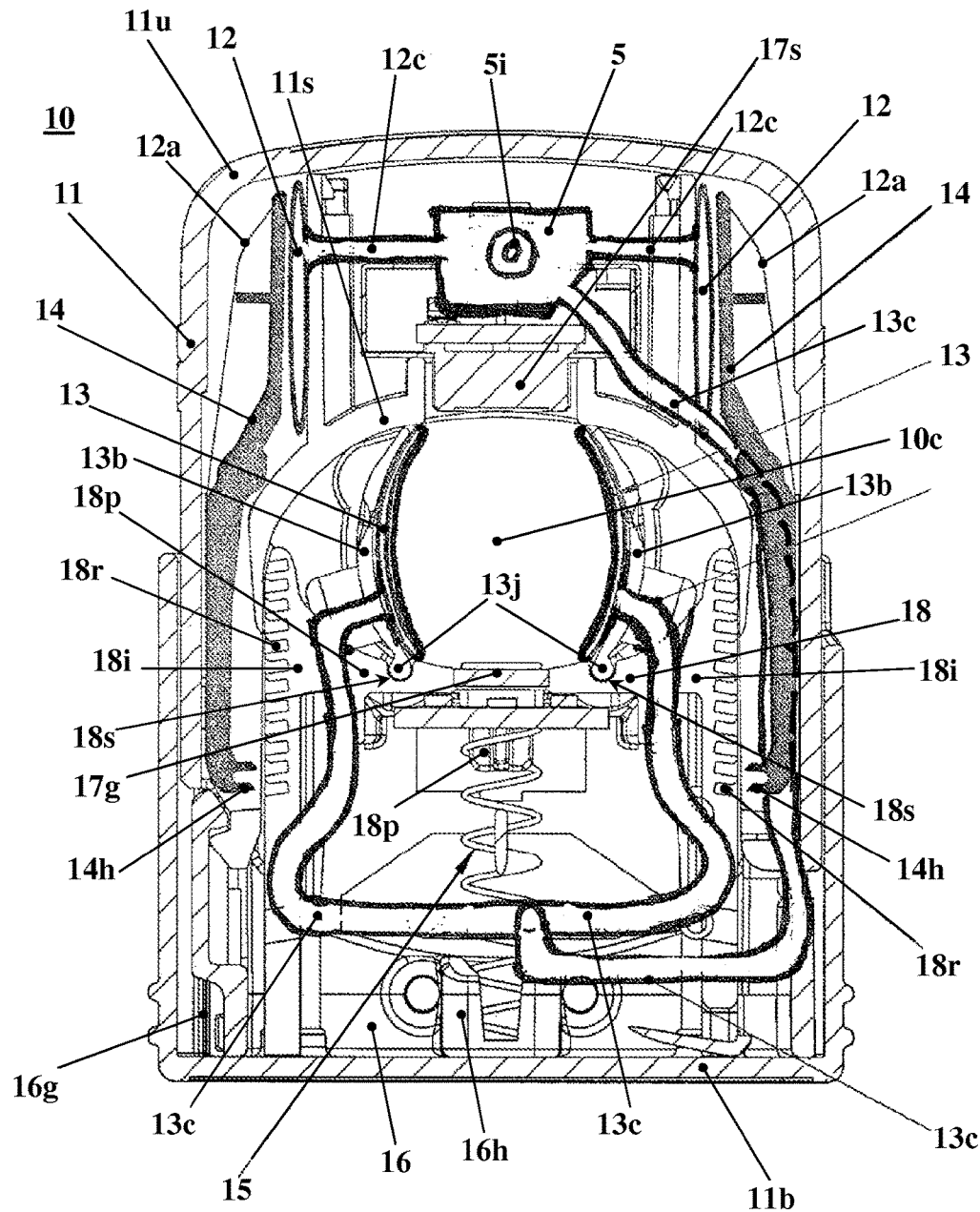
FIG. 2 shows a sectional view of the probe depicted in FIG. 1 in a non-engaged state.

Referring now to FIG. 2, wherein there is shown a sectional view of the probing device 10 taken along line A-A shown in FIG. 1. FIG. 2 demonstrates a possible mechanism usable for applying various pressure conditions over the finger tissue enclosed in the annular cavity 10c and carrying out the measurements on the enclosed finger tissue in predefined blood conditions caused due to the applied pressures. The sectional view shown in FIG. 2 depicts the probing device 10 in a non-engaged state (also referred to herein as unlocked state) i.e., prior to bringing the device into operating position with respect to pressure applied to the finger (e.g., prior to placing the finger in the probing cavity). Typically, in this unlocked state of the probing device 10 there is no application of pressures, except for some relatively weak pressure applied by spring 15.

In possible embodiments of the present application the probing device 10 includes one or more inflatable occluding cushions 13 (shown in a deflated state in FIG. 2), adapted to inflate and apply pressures over the finger tissue located in the cavity 10c. The occluding cushions 13 may be mounted on movable members 13b configured to adapt the location of the occluding cushions 13 and thereby enable to adjust the size of the annular cavity 10c to the size of the finger phalange positioned thereinside.

For example, in the embodiment shown in FIG. 2 two arc-shaped movable members 13b carrying the occluding cushions 13 are pivotally attached to a tray member 18 at two lateral opposing sides of the cavity 10c, thereby defining the size of the cavity 10c in the unlocked state. Movable members 13b may be hinged to the tray 18 by hinges 13j formed at their bottom ends and adapted to be received and held inside respective sockets 18s formed on upper side the tray 18. The tray 18 may be fixedly attached inside the housing 11 of the probing device 10.

A movable plate 16 provided at the bottom of housing 11 may be movably coupled by spring 15 to an upper portion 11u of the housing 11, and configured and operable to slide inside the housing 11 over linear guides 16g (better seen in FIG. 3) configured to permit upward and downward movement of the movable plate 16. More particularly, spring 15 may be attached at an upper end thereof over a supporting tooth 18p fixedly coupled to a bottom portion 11b of the housing 11, and at its other (lower) end it may be retained in a holding socket 16h provided on the upper side of the movable plate 16.

Figure 3:
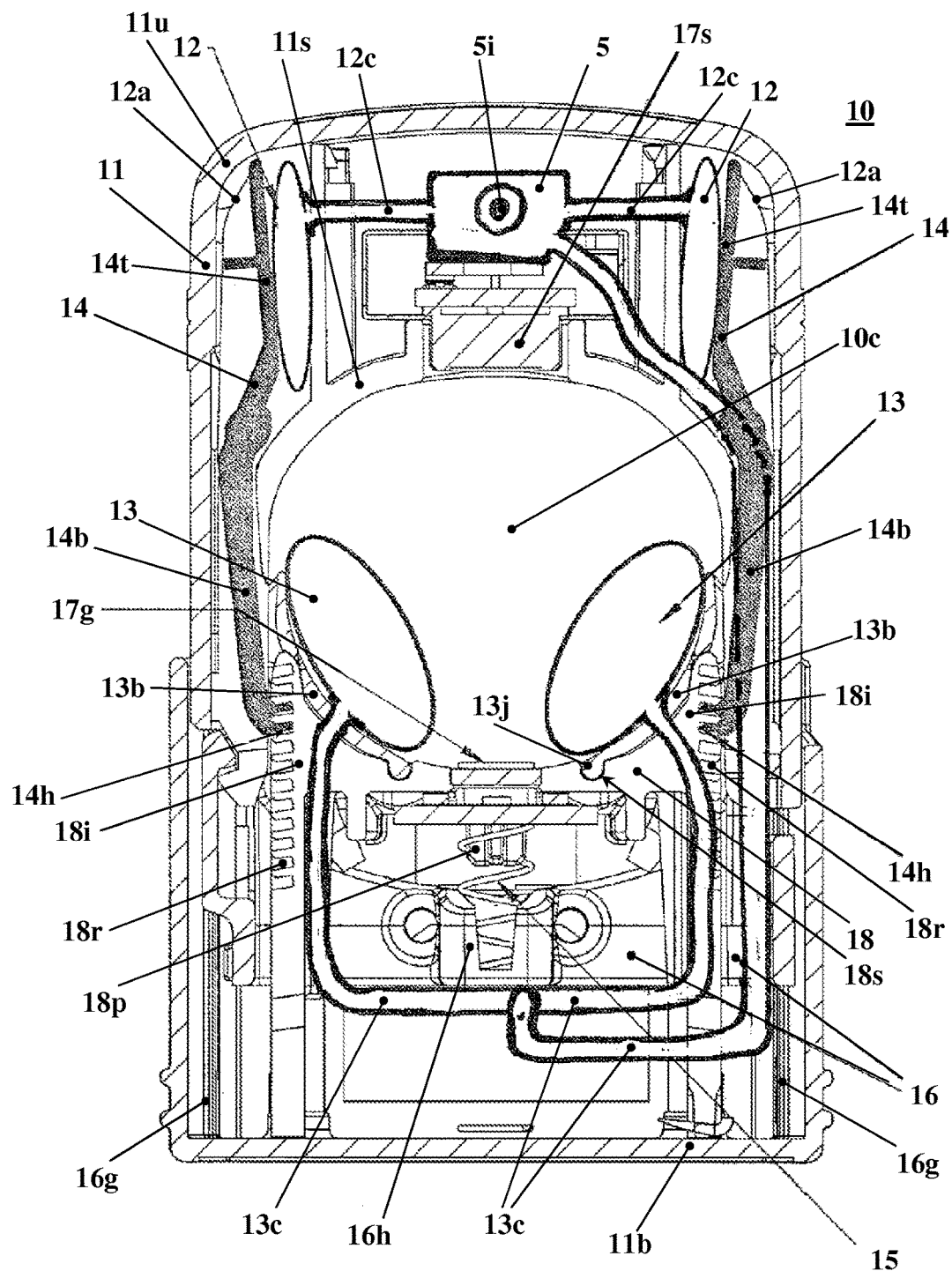
FIG. 3 shows the sectional view of the probe of FIG. 1 in an engaged state.

The housing 11 may be assembled from the bottom hollow portion 11b and the upper hollow portion 11u being configured to telescopically slide one relative to the other. The movable plate 16 may be fixedly attached to the upper hollow portion 11u of the housing 11, and coupled to the bottom portion 11b, by one or more elastic elements such as the spring 15. As seen in FIGS. 2 and 3 the movable plate 16 and the upper portion 11u of the probe are configured to slidably move together up and down within housing 11 relative to the bottom hollow portion 11b. The upper hollow portion 11u comprises a support member 11s fixedly attached thereinside, such that the height of the annular cavity 10c is defined by the distance between the support member 11s and the tray 18. In this way, the size of the annular cavity 10c may be adjusted to allow insertion of fingers of different sizes thereinto by pushing the upper hollow portion 11u upwardly, while inserting finger 7 into the cavity 10c, and simultaneously laterally pushing the two movable members 13b carrying the occluding cushions 13 in sideway directions (see FIG. 3).

Probing device 10 further comprises a locking mechanism configured to lock the upper portion 11u of the housing and the movable plate 16 attached to it in their position after a phalange of finger 7 is inserted thereinto. The locking mechanism may include one or more expandable members (e.g., inflatable balloons) 12 configured to controllably push one or more lever arms 14 configured for engaging immobilizing arms 18i, fixedly attached to the bottom hollow portion 11b, and hold them immobilized in their position. For example and without being limiting, the probing device 10 may include two expandable members 12 communicating via conduits 12c with a pressure supply manifold 5 which receives its pressure supply from an auxiliary system (40, described herein below with reference to FIG. 4) via a pressure inlet 5i. Pressure inlet 5i may be coupled to the male connector 11c and is further used as a pressure outlet whenever pressure is being discharged out of probing device 10.

With reference to FIG. 3, showing the probing device 10 in a locked state (i.e., engaged state), whenever fluid (e.g., air) pressure is applied via the pressure supply manifold 5 the expandable members 12 are inflated and push the upper portions 14t of lever arms 14 in sideway directions towards the walls of housing 11. The bottom portions 14b of lever arms 14 includes one or more stopper teeth 14h adapted to be received in retaining slots 18r provided along the immobilizing arms 18i fixedly connected to the sides of the sliding tray 18. In this way, as the upper portions 14t of lever arms 14 are pushed in sideway directions, their bottom portions 14b are pushed inwardly towards the immobilizing arms 18i such that the stopper teeth 14h become engaged in the retaining slots 18r, thereby locking the upper portion 11u of the housing and the movable plate 16 attached to it in their location.

FIG. 3 also shows the occluding cushions 13 in an expanded state. In this non limiting example, fluid pressure is supplied to the occluding cushions 13 from the supply manifold 5 via conduits 13c, thereby inflating them into the expanded state. In such possible embodiments the expandable members 12, which are relatively small (e.g., having volumes of about 0.1 to 1 cc), are located near the supply manifold 5, such that upon application of fluid pressures via supply manifold 5 the expandable members 12 become fully inflated before occluding cushions 13, and thereby lock the sliding tray 18 in its position before applying occluding pressure on the finger 7. Thereafter, further fluid pressure may be supplied via the supply manifold 5 to expand the occluding cushions 13, while the tray member 18 is immobilized, and thereby apply any desirable pressure conditions over the tissue of finger 7 located inside the annular cavity 10c.

For example, in some possible embodiments two expandable members 12 are used, each having a volume of about 0.05 cc (together about 0.1 cc) in the unexpanded state, and a volume of about 0.5 cc (together about 1 cc) in the expanded state.

Expandable members 12 may be configured as inflatable balloons made from any suitable type of deformable, flexible or elastic material, such as, but not limited to, polyethylen. Occluding cushions 13 may be configured as inflatable cuffs each having a maximal inflated volume of about 0.5 to 1 cc, optionally about 0.6 cc, and made of a type of flexible/elastic material, such as, but not limited to, polyethylen. The pressures applied and maintained via supply manifold 5 during the occlusive state in the measurement sessions may generally be in the range of 180 to 250 mmHg.

Probing device 10 further includes an optical assembly, including a light source 17g (emitter(s) or light guide associated with external emitter(s)) and a light detector 17s, which are adapted to illuminate a measurement location with one or more different wavelengths and detect the light response (transmittance/reflectance) of the illuminated measurement location. For example, in FIGS. 2 and 3 the light source device 17g is fixedly mounted on (or in) the upper side, and more or less at the center, of the sliding tray 18, and the light detector 17s is fixedly mounted in support member 11s defining the upper side of the cavity 10c. In this non limiting example, the light detector 17s is adapted to measure the intensity of light transmitted through the measurement location in response to illumination. However, other configuration of the optical assembly suitable for measuring light transmittance/reflection through/from an examined tissue may be used without departing from the scope and spirit of the present disclosure.

Light source device 17g may include a multi-wavelength light source and possibly also a spectral filtering assembly (not shown), adapted to produce light in the spectra required for carrying out the measurements. Alternatively, light source device 17g may include one or more separate light sources (not shown, e.g., light emitting diodes—LEDs) adapted to produce light in the desired wavelengths spectra respectively. For example and without being limiting, in possible embodiments of the present application, light source device 17g includes 8 LEDs used for emitting light in different wavelengths generally in the range of 600 to 1000 wavelengths.

After carrying out one or more measurement sessions the pressure is discharged from the expandable members 12 and the occluding cushions 13 via inlet 5i of the supply manifold 5. As the pressure is released from the expandable members 12, the return springs 12a push upper portions 14t of lever arms 14 inwardly back to their unlocked state. Simultaneously, the bottom portions 14b of lever arms 14 are pushed in sideways directions and thereby release the grip of their stopper teeth 14h over the immobilizing arms 18i. After the pressure is released from the occluding cushions 13, finger 7 may be removed from the cavity 10c, and once the stopper teeth 14h are removed from the retaining slots 18r the movable plate 16 is pushed downwardly by spring 15 thereby also pushing the upper hollow portion 11u downwardly back to the unlocked state shown in FIG. 2.

In some possible embodiments the tray member 18 is configured as a movable element that can be pressed downwardly against pressure applied by the spring 15. For example and without being limiting, the housing 11 may be configured without any movable parts (e.g., by fixedly attaching upper portion 11u of the housing to its bottom portion 11b) and the tray member 18 may be coupled to the housing by the spring 15 and configured to slide over the guiding members to adjust the dimensions/size of the cavity 10c to the size/dimensions of the finger 7. Other configurations providing a suitable mechanism for adjusting the size/dimension of the cavity 10c are also within the scope of the present invention.

Figure 4:
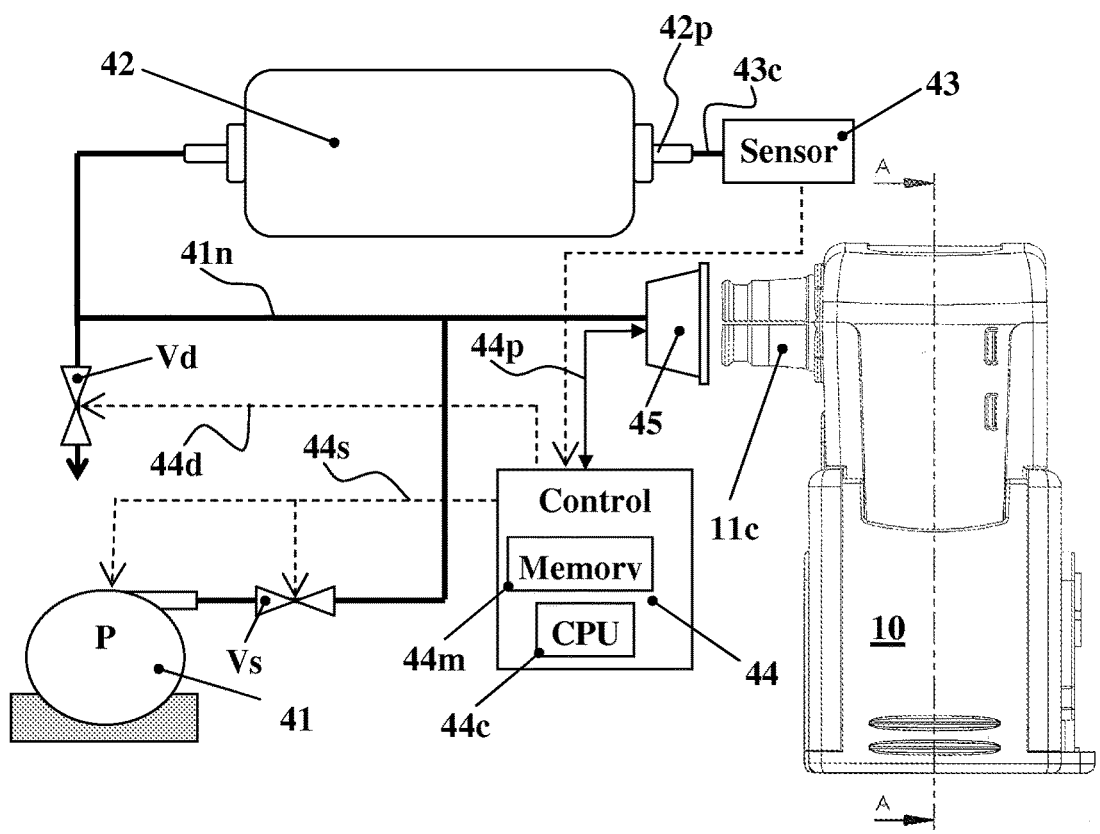
FIG. 4 demonstrates an auxiliary system for use with the probing device of FIGS. 1 to 3 according to some possible embodiments of the present disclosure.

A possible embodiment of the external auxiliary system 40 of the present application, usable for operating the probing device 10 and carrying out one or more measurement sessions therewith, is shown in FIG. 4. Auxiliary system 40 and probing device 10 are interfaced via (female) connector 45 configured to engage with the respective (male) connector 11c of probing device and thereby provide it the connectivity required to communicate electric signals over electric cable 44p and fluid pressures via conduit 41n. Alternatively, the auxiliary system 40 and the probing device 10 may be configured to wirelessly communicate electric signals using any suitable wireless communication technique (e.g., IR or RF, such as Bluetooth ZigBee or the like).

Auxiliary system 40 may include a pressure source (e.g., fluid pump) 41 connected to supply conduit 41n via controllable valve Vs, a pressure vessel 42 adapted to receive pressurized fluids via supply conduit 41n, a pressure sensor 43 for measuring the fluid pressure in the system, a discharge valve Vd connected to supply conduit 41n for discharging fluid pressures from the system, and a control unit 44. The control unit 44 is configured to communicate signals with the probing device 10 via electric cable 44p (or wirelessly), to receive signals from the pressure sensor 43, and to issue control signals 44s and 44d to control the states of the controllable valves Vs and Vd and to operate pressure source 41, respectively.

Discharge valve Vd may be a type of normally closed valve which may be changed into an open state after each measurement session. The pressure supply valve Vs may also be a normally closed valve which state is changed into an open state when the pressure source 41 is operated. It is however clear that any other suitable configuration of controllable (or manually operated) valves may be adopted for operation of system 40.

Figure 5:
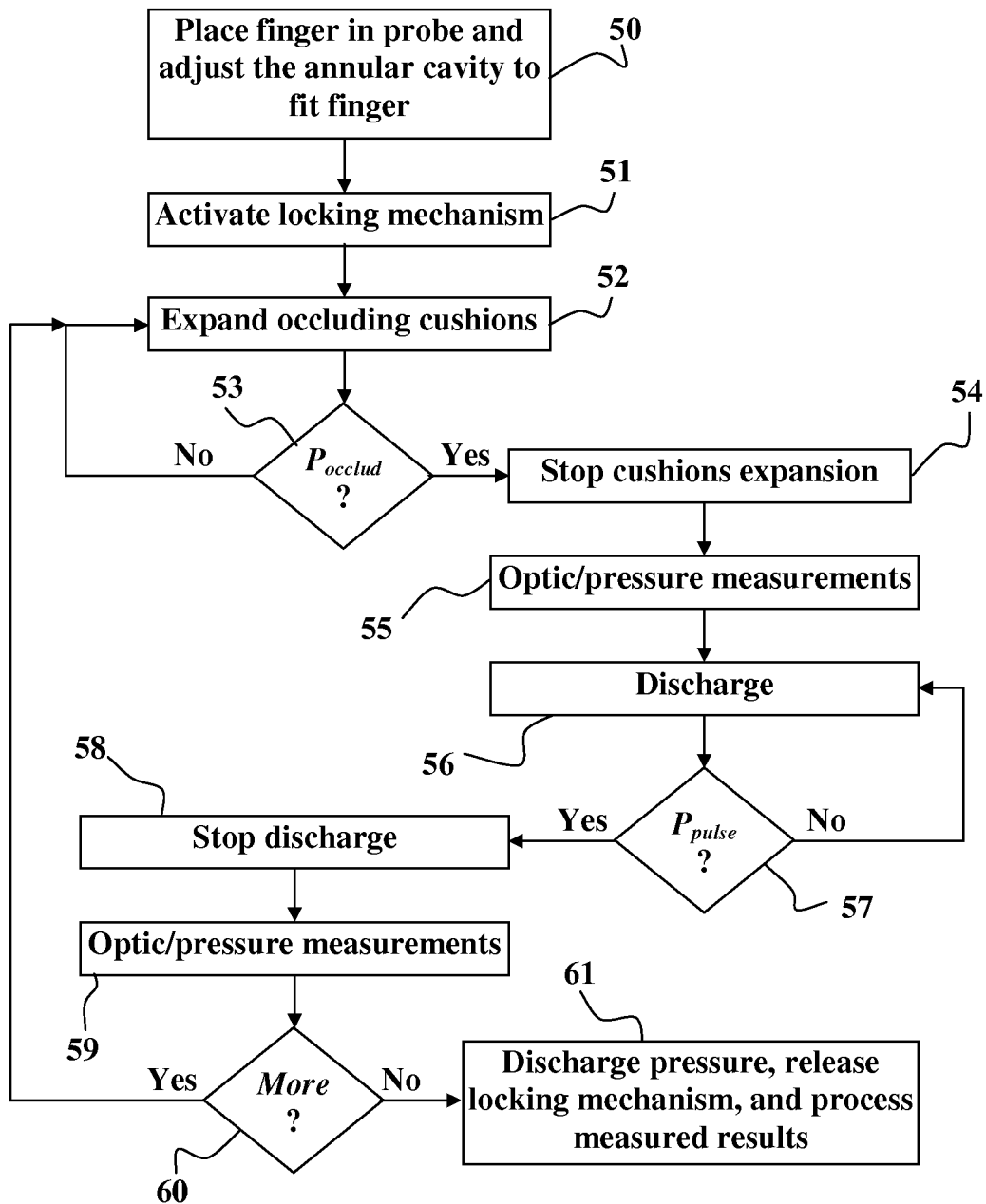
FIG. 5 is a block diagram demonstrating a process for carrying out measurements with the system illustrated in FIG. 4.

A possible measurement session is exemplified in the flowchart of FIG. 5. The measurement session is commenced in step 50 by placing finger 7 in the measurement position (i.e., inside the cavity 10c of probing device 10) and thereby adjusting the orientation of the movable members 13b carrying the occluding cushions 13 and the location of the upper portion 11u of the housing and the movable plate 16 attached to it to an engaged position. Next, in step 51, control unit changes valve Vs into its open state and activates the pressure source 41 to supply fluid pressure via conduit 41n to the supply manifold 5 of probing device 10 and to the pressure vessel 42, to thereby inflate expandable members 12 and lock the sliding tray 18 in the engaged position.

The control unit 44 may be configured to continuously or periodically measure the pressure in the system via pressure sensor 43 and determine accordingly if the probing device 10 changed into its locked state. In some possible embodiments the control unit 44 may be adapted to carry out one or more pulsatile optical and/or pressure measurement sessions on the finger 7 while in the locked state i.e., without applying occluding pressures by occluding cushions 13, by changing the state of supply valve Vs into its closed state and deactivating the pressure source 41.

Alternatively, control unit 44 may be adapted to proceed in step 52-53 with the pressure supply provided by the pressure source 41 to increase the pressure in the system up to an occluding pressure ($P_{ocllud}$ e.g., in the range of 180 to 250 mm Hg), in which the occluding cushions are inflated to effectively occlude and substantially stop the blood flow through finger 7. Once the occlusion pressure is reached, in step 54 the control unit changes the state of supply valve Vs into its closed state, deactivates the pressure source 41, and carries outs in step 56 various occlusive optical and/or pressure measurement sessions. For example, control unit 44 may be configured to sequentially activate light emitting device 17g to emit one or more light signals of different wavelengths, and responsively measure the intensity of the light transmitted through the finger tissue as detected by the light detector 17s, while in the occlusive state. Control unit 44 may be configured to further measure pressure changes in the inspected tissue while in the occlusive state, as reflected by pressure changes in the system measured by pressure sensor 43. The measured data may be processed to provide measurement optical and pressure data, which may be used to calculate various blood parameters. Alternatively, the measurement optical and pressure data may be recorded in a memory 44m (e.g., provided in the control unit 44, or in an external volatile/non-volatile memory) for later processing.

After completing the occlusive optical and/or pressure measurement sessions, in steps 56-57 the control unit 44 changes the state of discharge valve Vd into its open state to discharge and reduce fluid pressure in the system to a pulsatile pressure level ($P_{pulse}$ e.g., in the range of 30 to 70 mm Hg). Once the pulsatile pressure level is reached, in step 58 the control unit 44 changes the state of the discharge valve Vd into its closed state, and in step 59 carry out various pulsatile optical and/or pressure measurements. The measured data may be processed to determine various blood parameters, or recorded in memory 44m for later processing.

The control unit 44 may be adapted to determine the validity of the measured signals and responsively decide whether further measurements should be carried out using different occlusive and/or pulsatile pressures, and/or different wavelength spectrums. Accordingly, if it is determined that further measurements are needed, the control is passed in step 60 back to step 52. Alternatively, if the measured signals appear to be valid and suffice, the control is passed to step 61 wherein the control unit 44 changes the state of the discharge valve Vd into its open state to discharge the fluid pressure from the system until the locking mechanism of the probing device 10 is released, thereby to permit removal of finger 7 from the annular cavity 10c. The control unit 44 may be further configured to process and analyze the measurement data, and/or transfer the measurement data to an external data processing device (e.g., DSP unit, processing unit, or personal computer), and/or display measurement data and/or determined blood properties in a display device (e.g., LCD or CRT display—not shown).

The control unit 44 may be implemented by any suitable type of controller or data processor (e.g., FPGA, ASIC, PLC) comprising a processor 44c and one or more memories 44m (e.g., RAM, ROM, FLASH). In possible embodiments the control unit 44 is implemented using a personal computer (PC).

In some possible embodiments of the present application the probing device 10 is utilized to continuously measure the time dependent light radiation intensity, $I_\lambda(t)$ transmitted through (or reflected from) the examined tissue, for each applied light signal having a predetermined (or reference) wavelength λ. The auxiliary system 40 is adapted to measure pressure changes P(t) in the inspected tissue via the inflatable occluding cushions 13 of the probing device 10. For example, these pressure changes P(t) may be measured using a highly sensitive pressure sensor 43, which may be located inside pressure vessel 42, in one or more conduits, in the inflatable occluding cushions 13.

In some possible embodiments of the present application the pressure sensor 43 may be (e.g., pneumatically or hydraulically) coupled to pressure vessel 42 e.g., via an independent conduit 43c configured to couple the pressure sensor 43 to the pressure vessel 42 via a dedicated pressure sensing port 42p. In this way the pressure changes sensed by the inflatable occluding cushions 13 are communicated via the supply conduit 41n to the pressure vessel 42 and sensed by the pressure sensor 43 coupled to it.

In this non limiting example, the pressure vessel 42 contains a large portion (70-80%) of the overall volume of the system. There might be small variations in the overall volume due to variation in the size of the examined finger 7, movement of the finger or tubes, manufacturing etc. These variations become less important with the inclusion of the vessel because their relative magnitude is small in comparison with the total volume of the system. Therefore, by configuring the system such that a substantial portion of the overall volume of the system is provided by the pressure vessel, the total volume in different measurement sessions (e.g., due to different finger sizes) or probes is very similar, and universal calibration is therefore feasible and more effective.

In addition, the pressure applied and maintained by the pressure source 41 is more stable and less affected by small movements or leakages when the total volume is enlarged due to the pressure vessel 42. Thus, long term pressure deviations (e.g., due to improper orientation of the probe, inaccuracies of the pressures supplied by the pressure source 41, and suchlike) become negligible and not noticed in the measurement data due to the enlarged volume of the system provided by the pressure vessel 42. It is noted that this volume enlargement provided by the pressure vessel 42 is not so effective in removal of motion artifacts caused due to abrupt displacements/movements of the examined tissue, of the probe 10, and/or its movable elements, as discussed hereinbelow.

The conduits and inflatable members/cushions in auxiliary system 40 and in the probing device 10 are designed to minimize the total volume of the conduits and to thereby enable sensing relatively small pressure changes (e.g., in the range of Δ0.02 to Δ0.1 mm Hg) in the examined tissue via the occluding cushions 13 and communicating these pressure changes to the pressure sensor 43. The measured pressure changes may be used as indications of the volumetric blood changes in the finger of the examined subject. The measured pressure changes may be sued to determine low-perfusion (e.g., if the subject feels cold) or high-perfusion states in the examined finger, in which the signal to noise ratio may be significantly low, and correspondingly to ignore such measurements results and/or decide on corrective measures (e.g., carry out more measurements, change the pressure levels in the system, adjust the processing stage of the measurement data to substantially minimize or even remove interferences from the measured signals).

One major objective of the pressure vessel 42 is to provide pressure balancing and stabilizing to the pressure supply system, for example, by increasing the ratio of the total volume of the pressure system to the vasculature volume of the examined finger. This objective is mainly achieved due to the greater volume capacity of the pressure vessel 42 relative to the volumes of other members and components in the system (e.g., conduits, inflatable members/cushions). In this way, inaccuracies introduced in the examined fingers 7 having different volumes and sizes of different subjects (e.g., adults and children) are substantially canceled and their influences on the measured pressure signals become negligible. This configuration also helps to substantially minimize/cancel pressure changes that may be introduced due to movements of the examined finger 7 within the probing device 10.

For example, in order to use the pressure changes measured in the determination of Hemoglobin levels in the blood in the examined tissue the amount of pressurizing fluid in the system should be more or less constant. Therefore, pressure fluctuations which may be introduced due to finger movements and destabilize the pressures in the system should be minimized, and if possible canceled. The use of the pressure vessel 42 in system 40 therefore stabilizes the pressure system, substantially reduce/cancel interfering pressure fluctuations, and permits assuming that the volume of pressurizing fluids in the system is more or less constant.

In some possible embodiments the total volume of the conduits 12c and 13c, and supply manifold 5 (including that of any external cable connected via connectors 11c and 45) may generally be in the range of 1.5 to 3.5 cc, optionally about 2.5 cc, the volume of pressure vessel 42 may generally be in the range of 6 to 10 cc, optionally about 8 cc, and the total volume of the conduits (e.g., 41n and 43c) in the auxiliary system 40 may generally be in the range of 0.3 to 1.3 cc, optionally about 0.8 cc.

In some possible embodiments of the present disclosure a barometer and/or temperature sensor are also used in the probing device 10 and/or auxiliary system 40. In this way it is possible to add barometric measurements of the environmental atmospheric pressure and enable compensation of its effect on the internal pressure. Similarly, the temperature sensor enables corrections of temperature variations.

AC/DC Ratio

The relative change ΔI of the transmitted/reflected light intensity $I_\lambda$ from the inspected tissue measured in a given time interval $[t_a, t_b]$, may be defined as follows:

$$\Delta I / I(\lambda) = \frac{I_\lambda(t_b) - I_\lambda(t_a)}{I_\lambda(t_a)} \quad (1)$$

In a similar manner, the relative pressure change ΔP measured via the occluding cushions 13 (i.e., associated with the inspected tissue) may be expressed as follows:

$$\Delta P / P = \frac{P(t_b) - P(t_a)}{P(t_a)} \quad (2)$$

The AC/DC ratio is a common notation for the relative change when $t_a$ and $t_b$ are chosen as extreme points of the measured intensity of the light radiation transmitted/reflected through/from the examined tissue.

In occlusion signals, the AC/DC ratio is usually calculated over a cure ascending time period between the time of onset of occlusion and the time in which the measured light intensity reaches an asymptotic maximum, but there are other possible AC/DC ratios options that may be used as well, e.g., between the maximum and the end of occlusion (between the point where maximum pressure is applied and the end of curve.). In pulse signal measurements, for example, the AC/DC ratio may be calculated between time points associated with a minimum and a maximum of the light intensity of each single pulse modulation, and averaged over all pulses. Accordingly, the AC/DC ratio may be computed from the optical measurement data, from the pressure measurement data, or from a combination of the optical and pressure measurement data.

Parametric Slope

In some possible embodiments of the present disclosure, in order to translate the measured light intensity signal $I_\lambda$ into a normalized parameter, independent of geometry, the so called parametric slope (PS) is utilized. For two different light signals of wavelengths $\lambda$ and $\lambda_r$ (e.g., using a pair of light emitting diodes—LEDs), the PS is defined as the average ratio between their relative changes of signal intensity:

$$PS(\lambda, \lambda_r) = \frac{\Delta I_\lambda / I_\lambda}{\Delta I_{\lambda_r} / I_{\lambda_r}} = \frac{\Delta \log I_\lambda}{\Delta \log I_{\lambda_r}} = \frac{\partial \log I_\lambda}{\partial \log I_{\lambda_r}} \quad (3)$$

The wavelength $\lambda_r$ is used as a reference wavelength and is selected so as to maximize the correlation of the PS with the calculated analyte (it is desirable that at least some of the PS's be strongly correlated with the analyte concentration e.g., hemoglobin). The ratio in equation (3) above may be averaged over time to obtain a stable PS parameter.

For pulse signals, the averaging can be performed over the full measurement or only in the ascending/descending sections (diastole/systole) of the measured signals. In occlusion, the averaging window can be carried out over the entire signal intensity ascending period, or during a partial interval thereof (that can be fixed or determined by the measurement conditions). In general, each wavelength can have its optimal averaging window.

In possible embodiments, in addition to the optical PS, the pressure changes measurements are used to calculate a "volumetric" PS, as follows:

$$PSV = \frac{\Delta P / P}{\Delta I_{\lambda_r} / I_{\lambda_r}} = \frac{\Delta \log P}{\Delta \log I_{\lambda_r}} = \frac{\partial \log P}{\partial \log I_{\lambda_r}} \quad (4)$$

In general, each PS, either optical or volumetric, may be calculated over a different averaging time window.

In some embodiments of the present disclosure, abnormal values of PS's, as well as of the AC/DC ratios, which provides an indication of substandard measurements, are used to detect and exclude unreliable results. For example, the abnormalities may be defined using the same data set used for the calibration. Ranges of PS may be selected that exclude outliers and cases of bad measurements. In addition, physical considerations about the value of PS may be also considered, e.g., optical PS are supposed to be positive but volumetric PS is negative.

More particularly, the measured pressure is highly sensitive to abrupt displacements/movements of the movable parts of the probe 10, of its housing 11, and/or of the finger 7 (motion artifacts). These abrupt displacements/movements may cause abnormal local values (spike signals) in the optical and/or pressure measurement data, and correspondingly in the volumetric AC/DC and PS. The presence of such abnormal local values/spike signals enables filtering out motion artifacts from the measurement data e.g., by excluding from the averaging computation, and/or from the measurement data, those parts that are associated with abnormal values/spikes of the AC/DC or PS. It is noted that the filtering is most efficient with the volumetric AC/DC or PS, but in some embodiments the optical AC/DC or PS may be also used as well, or instead.

Calibration Equation

The concentration of an analyte under consideration, e.g., Hemoglobin, may be computed using the following formula:

$$Hb = A_0 + A_1 \cdot PSp(\lambda_1) + A_2 \cdot PSp(\lambda_2) + \ldots + A_n \cdot PSp(\lambda_n) + A_v \cdot PSVp + B_1 \cdot PSo(\lambda_1) + B_2 \cdot PSo(\lambda_2) + \ldots + B_m \cdot PSo(\lambda_m) + B_v \cdot PSVo \quad (5)$$

where PSp and PSo are pulse and occlusion parametric slopes correspondingly, PSVp and PSVo are the corresponding volumetric parametric slopes, and $A_i$ and $B_i$ are the calibration coefficients (i=1, 2, . . . , n, v, is an indexing integer, and n and v are positive integer values). Though in this example equation (5) is a linear equation i.e., a linear combination of the parametric slopes, in general, it may contain higher order terms of any form. In possible embodiments, the parametric slopes PSp and PSo are obtained according to equation (3), and parametric slopes PSVp and PSVo are obtained according to equation (4), using the same reference wavelength $\lambda_r$ for of all of the slopes. It is however noted that in possible embodiments a different reference for PSV, and even for optical PS, may be used. In addition, in some possible embodiments one reference wavelength may be used for the occlusion state and another reference wavelength for pulsatile wavelength.

The calibration coefficients $A_i$ and $B_i$ may be determined by a multiple regression process using large data set from extensive in vivo trials that include healthy and unhealthy subjects with wide range of Hb values. The optimal combination of PS's may be chosen so that the analyte prediction is most accurate on the data set and, optionally, by the method of principal component analysis (PCA). These combinations have maximum sensitivity to Hb concentration, and are less affected by other variables such as Oxygen saturation and blood volume.

Physiological Interpretation of Pressure Variations

When the pressure source is not operating, the pneumatic system is closed and according to the Boyle-Marriotte law:

$$P \cdot V = k$$

where V is the system volume and k is a constant value. Taking a derivative, the following equation for relative changes is obtained:

$$\Delta P / P = -\Delta V / V \quad (6)$$

Accordingly, as long as the system is closed, any change in volume is related to a pressure change. Therefore, volumetric variations of blood vessels in the measurement site that change the volume of the cushions are measured by the pressure sensor.

Figure 6:
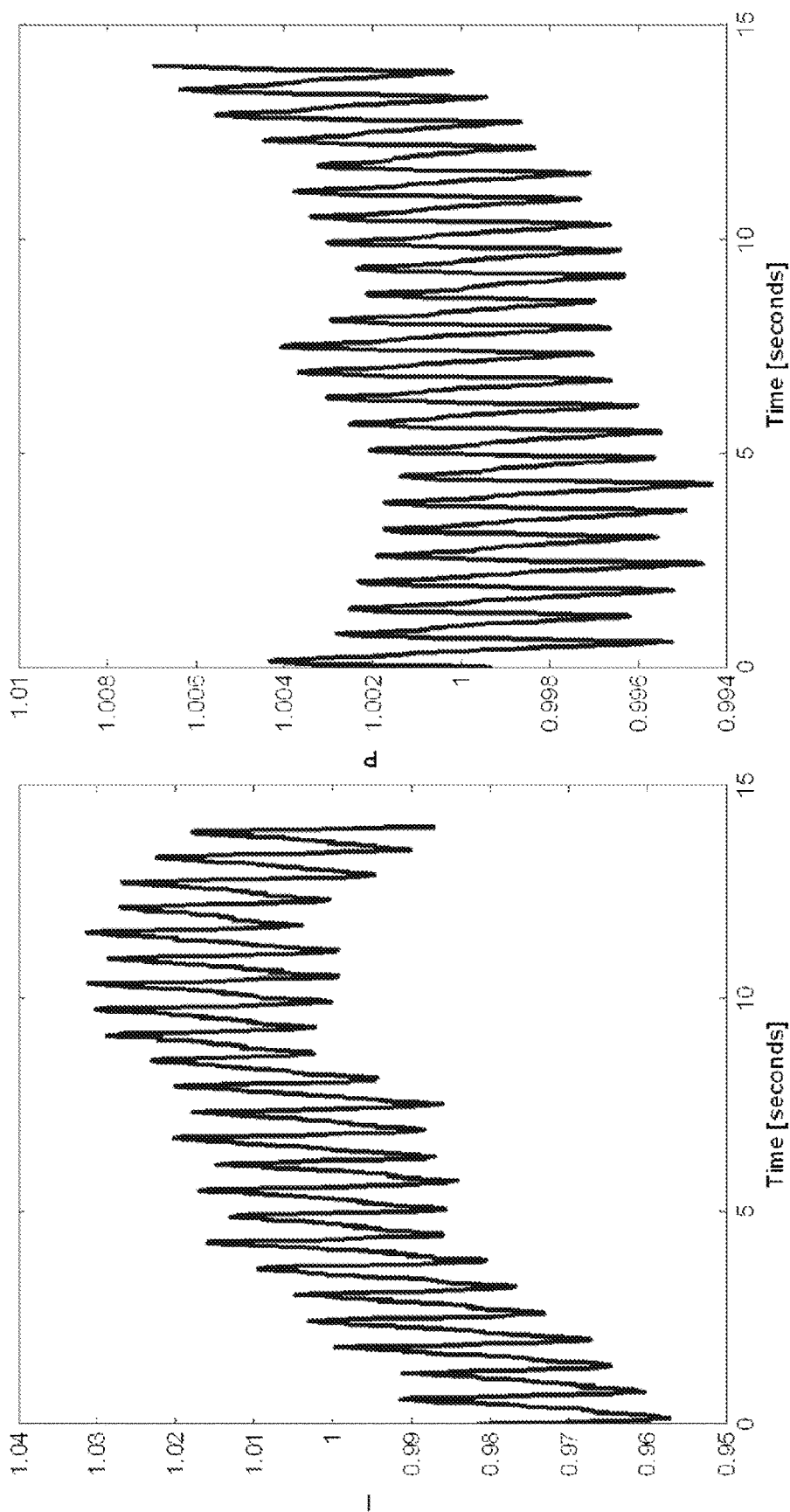
FIGS. 6A and 6B show respective line graphs of optical and pressure signals measured in a pulsatile blood state using an embodiment of the present disclosure.

FIG. 6A shows a graph line of an optical pulse signal (in normalized units) measured for emitted light signal in a wavelength of 630 nm (i.e., reflecting intensity changes of the light radiation transmitted through the examined tissue in normal blood pulsating conditions) and FIG. 6B shows a graph line of a pressure measurement taken simultaneously during the same pulsatile blood conditions. The graph lines shown in FIGS. 6A and 6B present data measured using an implementation of the system and probing device described hereinabove. As seen in FIGS. 6A and 6B the measured pressure signal exhibit significantly smaller relative changes over the measurement pulsatile time period. The relatively steady pressure measurements may indicate to the system that any volumetric changes which may have occurred during the measurement are negligibly small and that the determination of analyte concentration may be carried out assuming constant volumetric conditions in the system (e.g., if there is a large "jump" in the measured pressure it means unsteady volume and unreliable measurement).

Figure 7:
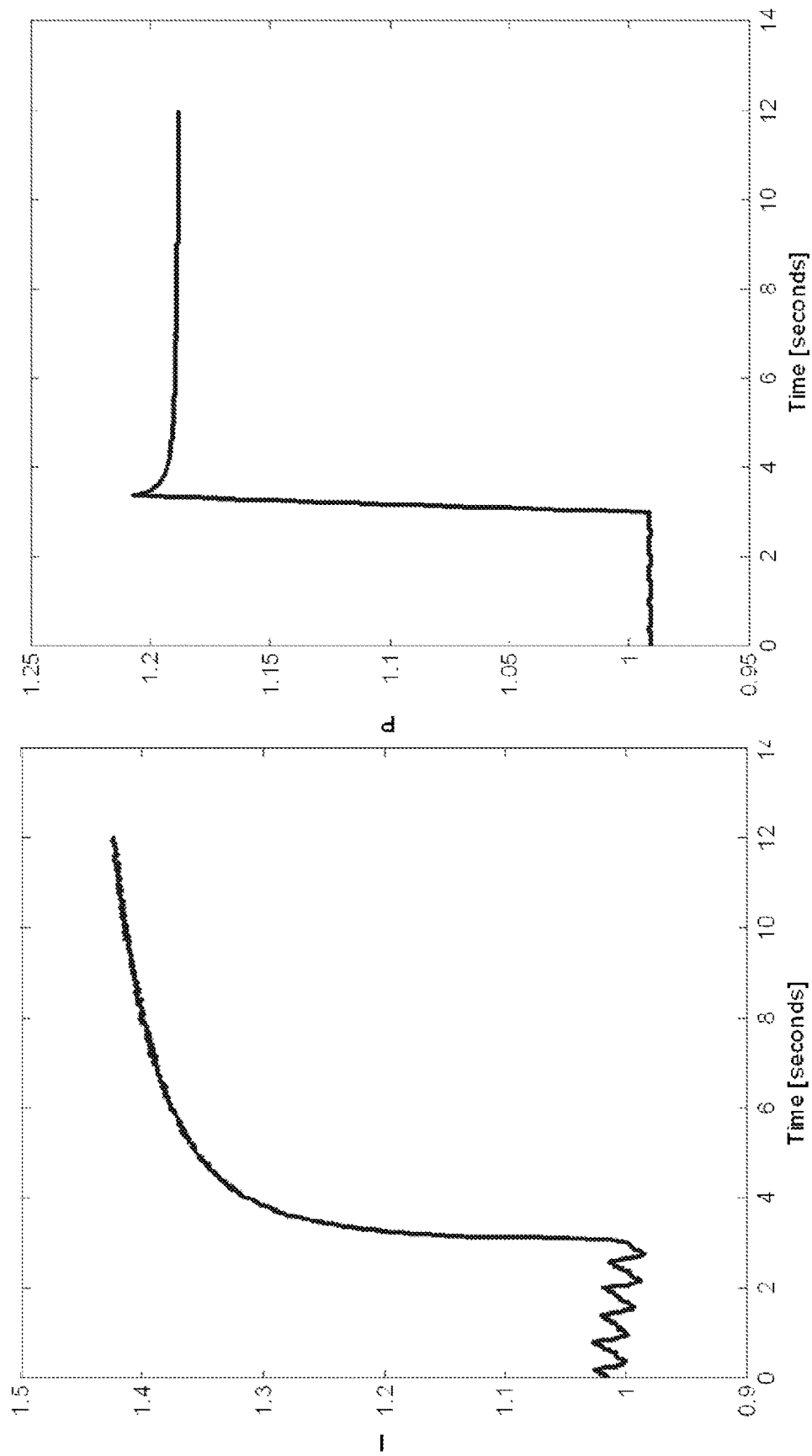
FIGS. 7A and 7B show respective line graphs of optic and pressure signals measured in an occlusive blood state with an embodiment of the present disclosure.

FIG. 7A shows a graph line of an occlusion optical signal (in normalized units) measured for emitted light signal of a wavelength of 630 nm (i.e., reflecting intensity changes of the light radiation transmitted through the examined tissue in occlusive blood conditions), and FIG. 7B shows pressure signals simultaneously measured during the same occlusive time period. As seen in FIGS. 7A and 7B, the blood pressure rapidly changes during the transition between the pulsatile and occlusive modes, and remains more or less constant during each of these states, thereby indicating on the pressure and volumetric stabilities which may be used to affirm the validity of the measured signals, and the validity of analyte concentration determined thereupon.

Performance Study

In this non limiting example, clinical study was conducted in the Hematology and Blood Bank Department of Assaf Harofeh Medical Center (Zerifin, Israel). Upon receipt of informed consent, two non-invasive Hemoglobin measurements were performed on the right and left thumbs of the subject. Reference Hb values were obtained from venous blood samples and evaluated on a Beckman Coulter LH 750 blood analyzer.

A total of 710 volunteers (348 male, 362 female) in the ages 18-69 years participated in the trial, yielding 1396 data pairs. Reference Hemoglobin values were in the range 5.3-17.5 g/dL and the values obtained by an implementation (i.e., combining measure optical and pressure signals as demonstrated in equation 5) were in the range 6.0-17.1 g/dL. The mean error (bias) of the readings obtained using this implementation compared to the reference data was 0.01 g/dL, and the accuracy, defined as the standard deviation of error, was 0.94 g/dL. The correlation was 0.89 and the mean absolute error was 0.76 g/dL.

Figure 8:
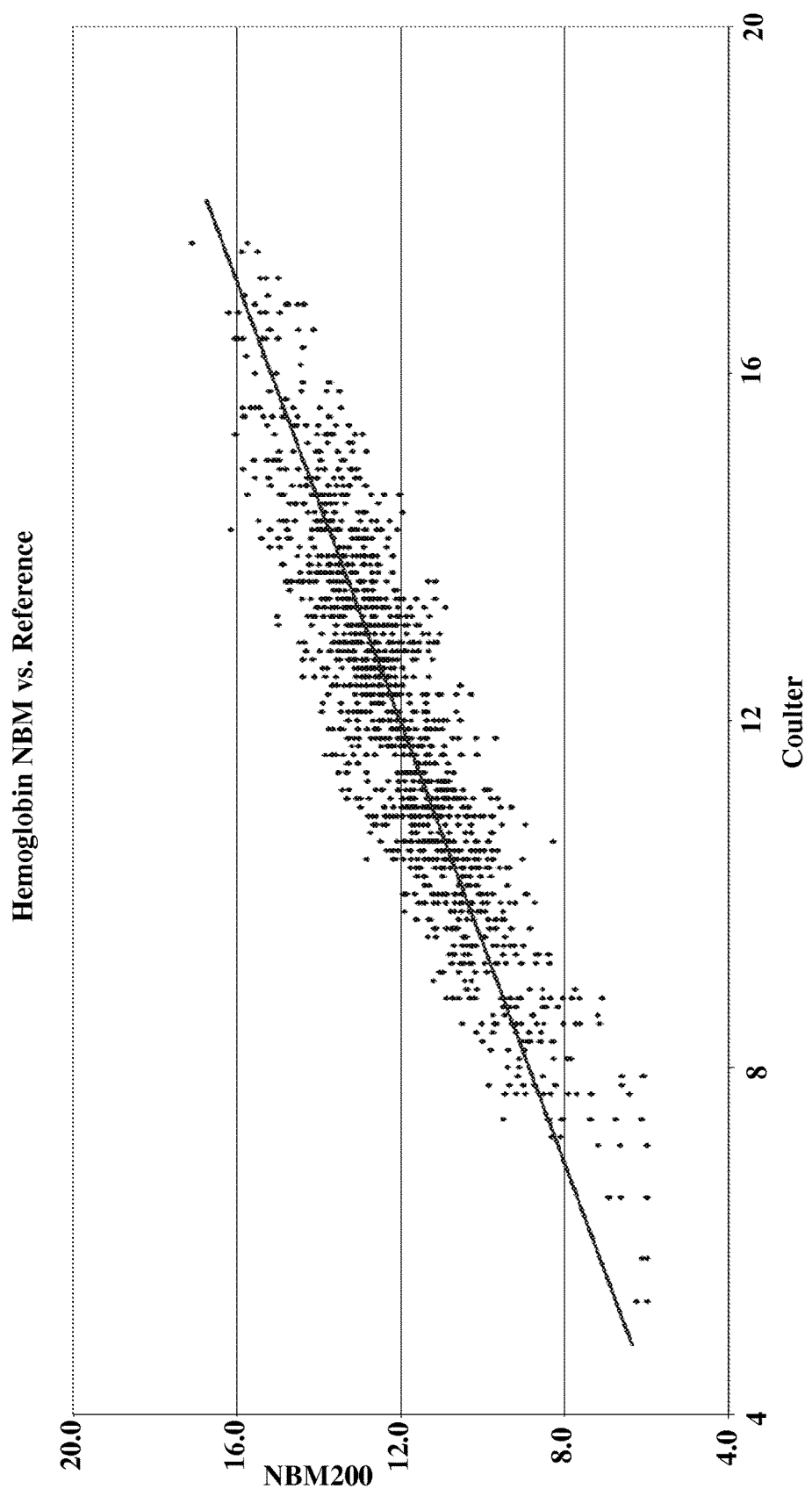
FIG. 8 show a dot chart of Hemoglobin readings taken using an embodiment of the present disclosure against conventional in vivo Hemoglobin measurements.

FIG. 8 is a scatter plot showing the Hemoglobin levels measured using the implementation of the present invention against the conventionally in vivo measurements of the Hemoglobin levels.

Some advantages of embodiments of the present application are listed below:
  Large variations comparing to regular pulse (AC/DC), namely, the signal variations during occlusion is much larger than in regular pulse.
  Smooth signals having improved signal to noise ratio.
  Time dependent physiology reveals more information.
  Selection of LEDs in a broad optical wavelengths range (550-1500 nm).
  Less motion artifact and better perfusion due to location on finger root.
  Uniformity of the finger between subjects. For example, the occlusions in similar pressure brings the fingers to more uniform situation than in normal pulse. For example, if it is cold and the finger shrunk the occlusions massage the finger and improve blood circulation.
  Better performance in low perfusion.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A system for measuring level of at least one analyte of a subject, the system comprising:
  a probe for attaching to the subject, said probe carrying an optical assembly configured and operable for applying optical measurements to a measurement location in the subject and generating optical measured data indicative thereof, the optical measurements comprising measurements taken from the measurement location in at least one of pulsatile and occlusive blood states;
  an auxiliary system comprising a pressure system configured and operable for controllably applying pressure to the subject in the vicinity of the measurement location and affecting at least one of said pulsatile and occlusive blood states at the measurement location, and a pressure sensor system in fluid connection with the pressure system for measuring changes of pressure inside the pressure system during the application of said pressure to the subject in the vicinity of the measurement location and generating pressure data, said pressure data being thereby indicative of the pressure changes in the pressure system caused by volumetric changes in the measurement location to which said pressure is being applied; and
  a control system configured and operable for receiving and processing the pressure data and the optical measured data, determining at least one relation between the optical measured data and the corresponding pressure data, and analyzing said at least one relation for determining the at least one analyte of the subject.

2. A system according to claim 1, wherein the pressure system comprises at least one expandable element carried by the probe and being configured and operable to be shiftable between its unexpanded and expanded states to thereby selectively permit said pulsatile blood state and create said occlusive blood state in the measurement location respectively.

3. A system according to claim 2, wherein the pressure system comprises a pressure source fluidly coupled to the at least one expandable element and configured and operable to apply a fluid pressure operable to shift said expandable element into the expanded state.

4. A system according to claim 3, wherein said pressure sensor system comprises a pressure vessel fluidly coupled to at least one of the pressure source and the at least one expandable element and configured and operable to hold a volume of pressurized fluid, such that pressure of the pressurized fluid in said pressure vessel changes in accordance with the volumetric changes in the measurement location to which said pressure is being applied.

5. A system according to claim 4, wherein a volume of the pressure vessel is greater than a summation of volumes of the at least one expandable element and of elements in the system coupled thereto, to thereby increase a ratio of pressure system volume to vasculature volume at the measurement location.

6. A system according to claim 5, wherein the volume of the pressure vessel is at least twice the summation of volumes.

7. A system according to claim 1, comprising a barometric pressure sensing element configured and operable to measure atmospheric pressure of an environment external to said system and generate barometric data indicative thereof, the control system is configured and operable to use said barometric data to compensate effects of said atmospheric pressure on the pressure measurement data.

8. A system according to claim 1 comprising a temperature sensor configured and operable to measure temperature at the measurement location and generate temperature data indicative thereof, the control system is configured and operable to use said temperature data to correct influence of temperature on at least one of the pressure and optical measurement data.

9. A system according to claim 1, wherein said probe defines a probing cavity for holding a body portion of the subject such as to bring a measurement location in said body portion into a measurement position, said probe being configured and operable to adjust a size of the probing cavity to geometry of said body portion.

10. A system according to claim 9 wherein the at least one expandable element is movably disposed inside the adjustable probing cavity.

11. A system according to claim 9, comprising a locking mechanism configured and operable to immobilize movable parts associated with the adjustable cavity to set said adjustable cavity into a locked state.

12. A system according to claim 11, wherein the locking mechanism includes at least one inflatable member fluidly coupled to a pressure source and configured and operable to receive fluid pressure therefrom and responsively change said locking mechanism into the locked state for immobilizing the movable parts and setting a desired size of said adjustable cavity.

13. A system according to claim 9 wherein the probe comprises a housing having bottom and upper hollow portions telescopically movable one relative to the other, movement of said hollow portions defines the size of the adjustable probing cavity, and wherein said locking mechanism is configured and operable to stop movement of said hollow portions in the locked state.

14. A system according to claim 13 wherein the housing comprises a movable plate fixedly coupled to the upper hollow portion and elastically coupled to the bottom hollow portion for applying pressure over the body portion held in the probing cavity.

15. A system according to claim 1 wherein the control system is configured and operable to validate the measured data based on at least one of the pressure and the optical measurement data.

16. A system according to claim 1 wherein the at least one analyte comprises at least one of hemoglobin and Oxygen saturation.

17. A system according to claim 1 wherein the determining of the at least one analyte by the control system comprises at least one of the following: determining an AC/DC ratio from either the optical measurement data or the pressure measurement data; and determining a parametric slope based on at least one of the optical measurement data and the pressure measurement data.

18. A system according to claim 1 wherein the control system is configured and operable to validate the measured data based on at least one of the following: an AC/DC ratio determined based on either the optical measurement data or the pressure measurement data; and a parametric slope determined based on at least one of the optical measurement data and the pressure measurement data.

19. A system according to claim 1 wherein the control system is configured and operable to determine the at least one analyte of the subject by computing a combination of the determined at least one relation between the optical measured data and the corresponding pressure data with a plurality of calibration coefficients.

20. A system according to claim 1 wherein the control system is configured and operable to determine the at least one analyte of the subject based on a parametric slope derived at least from the optical data.

21. A system for measuring level of at least one analyte of an examined tissue, the system comprising:
   at least one expandable element configured and operable to apply pressure to a vicinity of a measurement location on the tissue, to permit a pulsatile blood state in said tissue in an unexpanded state of the expandable element, and to apply an occlusive blood state in said tissue in an expanded state thereof;
   an optical assembly configured to detect light response of the measurement location to incident light and generate optical measurement data indicative of the detected light response, while the examined tissue is in at least one of said pulsatile and occlusive blood states;
   a pressure sensor fluidly coupled to said at least one expandable element and being configured and operable to generate pressure measurement data indicative of pressure applied to said at least one expandable element from said tissue being in at least one of said pulsatile and occlusive blood states; and
   a processor configured to process said pressure and optical measurement data, validate at least one of said optical and pressure measurement data based on at least one of the measurements data, and whenever it is determined that said data is valid calculate at least one relation between the optical and the pressure measurement data, said at least one relation being indicative of said at least one analyte of the examined tissue.

22. A method for measuring by a computerized device level of at least one analyte in a subject, said computerized device comprising at least one processor and one or more memories for storing instructions executable by said at least one processor and configured to carry out the following:
   operating a pressure system for applying pressure to the subject in the vicinity of a measurement location in the subject and affecting at least one of pulsatile and occlusive blood states at said measurement location;
   receiving from an optical assembly configured to communicate with said computerized device optical measured data taken from said measurement location while in said at least one of the pulsatile and occlusive blood states;
   receiving from a pressure sensor being in fluid connection with the pressure system and configured to communicate with said computerized device pressure data indicative of pressure changes inside the pressure system that are due to vascular volumetric changes in the measurement location in the subject while in the at least one of the pulsatile and occlusive blood states during which the optical measured data is obtained;

processing the optical measured data and the pressure data and determining at least one relation between said optical measured data and said pressure data; and determining said at least one analyte of the subject based on said at least one relation.

23. A method according to claim 22 wherein the processing of the measured data by the computerized device comprises validating the measured data based on at least one of the pressure data and the optical measured data.

24. A method according to claim 22 wherein the processing of the measured data by the computerized device comprises filtering artifacts from the measurement data based on at least one of the optical measured data and the pressure data.

25. A method according to claim 22 wherein the determining of the at least one analyte of the subject by the computerized device comprises determining at least one of the following: an AC/DC ratio from either the optical measurement data or the pressure measurement data; and a parametric slope determined based on at least one of the optical measurement data and the pressure measurement data.

26. A method according to claim 22 comprising determining at least one calibration coefficient based on data obtained in vivo from healthy and unhealthy subjects and using said at least one calibration coefficients in the determining of the at least one analyte.

27. A method according to claim 22 wherein the at least one analyte comprises at least one of hemoglobin and Oxygen saturation.

28. A method according to claim 22 wherein the processing of the measured data by the computerized device comprises validating the measured data based on at least one of the following: an AC/DC ratio determined based on either the optical measurement data or the pressure measurement data; and a parametric slope determined based on at least one of the optical measurement data and the pressure measurement data.

29. A method according to claim 22 wherein the computerized device is configured to operate the optical assembly to apply at least two light signals of different wavelengths through examined tissue at the measurement location while in the at least one of the pulsatile and occlusive blood states, and wherein the optical measured data is indicative of passage of the at least two light signals of different wavelengths through the examined tissue in the at least one of the pulsatile and occlusive blood states.

30. A method according to claim 29 wherein at least one of the wavelengths is a reference wavelength, and wherein the pressure data is indicative of vascular volumetric changes during application of light of said reference wavelength.

* * * * *